(12) United States Patent
Guy et al.

(10) Patent No.: US 10,849,860 B2
(45) Date of Patent: *Dec. 1, 2020

(54) USE OF CANNABINOIDS IN THE TREATMENT OF EPILEPSY

(71) Applicant: GW Research Limited, Cambridge (GB)

(72) Inventors: Geoffrey Guy, London (GB); Stephen Wright, London (GB); Orrin Devinsky, New York, NY (US)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/198,141

(22) Filed: Nov. 21, 2018

(65) Prior Publication Data

US 2019/0091171 A1 Mar. 28, 2019

Related U.S. Application Data

(63) Continuation of application No. 15/449,535, filed on Mar. 3, 2017, now Pat. No. 10,137,095, which is a continuation of application No. 14/881,969, filed on Oct. 13, 2015, now Pat. No. 10,111,840.

(30) Foreign Application Priority Data

Oct. 14, 2014 (GB) .................................. 1418171.3

(51) Int. Cl.
| | | |
|---|---|---|
| A61K 31/05 | (2006.01) | |
| A61K 9/08 | (2006.01) | |
| A61K 31/352 | (2006.01) | |
| A61K 45/06 | (2006.01) | |
| A61K 47/10 | (2017.01) | |

(52) U.S. Cl.
CPC ................ *A61K 31/05* (2013.01); *A61K 9/08* (2013.01); *A61K 31/352* (2013.01); *A61K 45/06* (2013.01); *A61K 47/10* (2013.01)

(58) Field of Classification Search
CPC .................................................... A61K 31/05
See application file for complete search history.

(56) References Cited

U.S. PATENT DOCUMENTS

| | | | |
|---|---|---|---|
| 6,383,513 B1 | 5/2002 | Watts et al. | |
| 6,403,126 B1 | 6/2002 | Webster | |
| 6,949,582 B1 | 9/2005 | Wallace | |
| 8,293,786 B2 | 10/2012 | Stinchcomb | |
| 8,603,515 B2 | 12/2013 | Whittle | |
| 8,673,368 B2 | 3/2014 | Guy et al. | |
| 9,017,737 B2 | 4/2015 | Kikuchi et al. | |
| 9,023,322 B2 | 5/2015 | Van Damme et al. | |
| 9,066,920 B2 | 6/2015 | Whalley et al. | |
| 9,125,859 B2 | 9/2015 | Whalley et al. | |
| 9,168,278 B2 | 10/2015 | Guy et al. | |
| 9,259,449 B2 | 2/2016 | Raderman | |
| 9,474,726 B2 | 10/2016 | Guy et al. | |
| 9,522,123 B2 | 12/2016 | Whalley et al. | |
| 9,949,936 B2 | 4/2018 | Guy et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 1,009,252 A1 | 10/2018 | Guy et al. | |
| 1,011,184 A1 | 10/2018 | Guy et al. | |
| 1,013,709 A1 | 11/2018 | Guy et al. | |
| 2004/0034108 A1 | 2/2004 | Whittle | |
| 2004/0049059 A1 | 3/2004 | Mueller | |
| 2004/0110828 A1 | 6/2004 | Chowdhury et al. | |
| 2005/0042172 A1 | 2/2005 | Whittle | |
| 2005/0266108 A1 | 12/2005 | Flockhart et al. | |
| 2006/0039959 A1 | 2/2006 | Wessling | |
| 2007/0060638 A1 | 3/2007 | Olmstead | |
| 2007/0099987 A1 | 5/2007 | Weiss et al. | |
| 2008/0119544 A1 | 5/2008 | Guy et al. | |
| 2008/0188461 A1 | 8/2008 | Guan | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0317729 A1 | 12/2010 | Guy et al. | |
| 2011/0028431 A1 | 2/2011 | Zerbe et al. | |
| 2011/0038958 A1 | 2/2011 | Kikuchi et al. | |
| 2011/0082195 A1 | 4/2011 | Guy et al. | |
| 2012/0004251 A1 | 1/2012 | Whalley et al. | |
| 2012/0165402 A1 | 6/2012 | Whalley et al. | |
| 2012/0183606 A1 | 7/2012 | Bender et al. | |
| 2012/0202891 A1 | 8/2012 | Stinchcomb et al. | |
| 2012/0270845 A1 | 10/2012 | Bannister et al. | |

(Continued)

FOREIGN PATENT DOCUMENTS

| | | |
|---|---|---|
| CA | 2737447 | 10/2012 |
| CA | 2859934 | 3/2016 |

(Continued)

OTHER PUBLICATIONS

[No Author Listed], "Missouri House passes cannabis extract legislation," Kansas City Star, 2014, https://kansascity.com/news/politics-government/article346747.html, 2 pages.

(Continued)

*Primary Examiner* — Kortney L. Klinkel
*Assistant Examiner* — Tori Strong
(74) *Attorney, Agent, or Firm* — Cooley LLP

(57) ABSTRACT

The present disclosure relates to the use of cannabidiol (CBD) for the treatment of atonic seizures. In particular the CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types. The disclosure further relates to the use of CBD in combination with one or more anti-epileptic drugs (AEDs).

32 Claims, 1 Drawing Sheet

(56) References Cited

U.S. PATENT DOCUMENTS

| | | |
|---|---|---|
| 2013/0143894 A1 | 6/2013 | Bergstrom et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2020/0000741 A1 | 1/2020 | Guy et al. |
| 2020/0069608 A1 | 3/2020 | Guy et al. |

FOREIGN PATENT DOCUMENTS

| | | |
|---|---|---|
| CN | 101040855 | 9/2007 |
| CN | 103110582 | 5/2013 |
| DE | 102012-105063 | 12/2013 |
| EP | 2448637 | 5/2012 |
| GB | 2384707 | 8/2003 |
| GB | 2434097 | 7/2007 |
| GB | 2434312 | 7/2007 |
| GB | 2450753 | 1/2009 |
| GB | 0911580.9 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| GB | 2487712 A | 10/2015 |
| GB | 2531282 | 4/2016 |
| GB | 2438682 | 12/2017 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/017892 A1 | 12/2006 |
| WO | WO 2006/133941 | 12/2006 |
| WO | WO 2007/083098 | 7/2007 |
| WO | WO 2007/138322 | 12/2007 |
| WO | WO 2008/019146 | 2/2008 |
| WO | WO 2008/094181 | 8/2008 |
| WO | WO 2008/129258 | 10/2008 |
| WO | WO 2008/144475 | 11/2008 |
| WO | WO 2008/021394 A2 | 12/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2010/012506 | 2/2010 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/032351 | 3/2013 |
| WO | WO 2014/146699 | 9/2014 |
| WO | WO 2015/142501 | 9/2015 |
| WO | WO 2015/184127 | 12/2015 |
| WO | WO 2015/187988 | 12/2015 |
| WO | WO 2015/193668 | 12/2015 |
| WO | WO 2016/059405 | 4/2016 |
| WO | WO 2016/084075 | 6/2016 |
| WO | WO 2016/118391 A1 | 7/2016 |
| WO | WO 2016/147186 | 9/2016 |
| WO | WO 2016/022936 | 11/2016 |
| WO | WO 2016/199148 | 12/2016 |
| WO | WO 2018/002636 | 1/2018 |
| WO | WO 2018/002636 A1 | 1/2018 |
| WO | WO 2018/002637 | 1/2018 |
| WO | WO 2018/037203 | 3/2018 |

OTHER PUBLICATIONS cdc.gov [online], "2 to 20 years: Girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj411022.pdf>, 1 page.

Chou, "Theoretical basis, experimental design, and computerized simulation of synergism and antagonism in drug combination studies," Pharmacol Rev., Sep. 2006, 58(3), 621-681.

Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.

Morelli et al., "The effects of cannabidiol and its synergism with bortezomib in multiple myeloma cell lines. A role for transient receptor potential Vanilloid type-2," Int J Cancer, Jun. 2014, 134(11): 2534-2546.

Nabissi et al, "Cannabinoids synergize with cafilzomib, reducing multiple myeloma cells viability and migration," Oncotarget, Oct. 2016, 7: 77553.

PCT International Preliminary Report on Patentability in International Appln. No. PCT/GB2017/052229, dated Feb. 26, 2019, 7 pages.

PCT International Search Report and Written Opinion in International Appln. No. PCT/GB2017/052229, dated Oct. 6, 2017, 10 pages.

Raab et al., "Multiple myeloma," Lancet, Jul. 2009, 374(9686): 324-339.

Velasco et al., "Anticancer mechanisms of cannabinoids," Curr Oncol, Mar. 2016, 23(2): S23-S32.

U.S. Appl. No. 13/380,305, filed Mar. 19, 2012, Benjamin Whalley.
U.S. Appl. No. 14/579,061, filed Dec. 22, 2014, Benjamin Whalley.
U.S. Appl. No. 15/346,844, filed Nov. 9, 2016, Benjamin Whalley.
U.S. Appl. No. 16/149,983, filed Oct. 2, 2018, Benjamin Whalley.
U.S. Appl. No. 13/977,766, filed Jul. 1, 2013, Benjamin Whalley.
U.S. Appl. No. 14/345,968, filed Mar. 20, 2014, Benjamin Whalley.
U.S. Appl. No. 14/741,783, filed Jun. 17, 2015, Geoffrey Guy.
U.S. Appl. No. 15/284,766, filed Oct. 4, 2016, Geoffrey Guy.
U.S. Appl. No. 15/449,084, filed Mar. 3, 2017, Geoffrey Guy.
U.S. Appl. No. 15/449,124, filed Mar. 3, 2017, Geoffrey Guy.
U.S. Appl. No. 15/449,185, filed Mar. 3, 2017, Geoffrey Guy.
U.S. Appl. No. 15/449,204, filed Mar. 3, 2017, Geoffrey Guy.
U.S. Appl. No. 15/449,177, filed Mar. 3, 2017, Geoffrey Guy.
U.S. Appl. No. 15/948,412, filed Apr. 9, 2018, Geoffrey Guy.
U.S. Appl. No. 14/881,954, filed Oct. 13, 2015, Geoffrey Guy.
U.S. Appl. No. 14/881,969, filed Oct. 13, 2015, Geoffrey Guy.

(56) References Cited

OTHER PUBLICATIONS

U.S. Appl. No. 15/449,402, filed Mar. 3, 2017, Geoffrey Guy.
U.S. Appl. No. 15/449,535, filed Mar. 3, 2017, Geoffrey Guy.
U.S. Appl. No. 14/741,829, filed Jun. 17, 2015, Geoffrey Guy.
U.S. Appl. No. 15/183,947, filed Jun. 16, 2015, Geoffrey Guy.
U.S. Appl. No. 15/519,233, filed Apr. 14, 2017, Geoffrey Guy.
U.S. Appl. No. 15/519,244, filed Apr. 14, 2017, Geoffrey Guy.
U.S. Appl. No. 15/640,033, filed Jun. 30, 2017, Jitinder Wilkhu.
U.S. Appl. No. 15/751,563, filed Feb. 9, 2018, Colin Stott.
U.S. Appl. No. 16/090,039, filed Sep. 28, 2018, Geoffrey Guy.
U.S. Appl. No. 16/314,583, filed Dec. 31, 2018, Stephen Wright.
U.S. Appl. No. 16/314,569, filed Dec. 31, 2018, Harshit Shah.
U.S. Appl. No. 16/328,209, filed Feb. 25, 2019, Colin Stott.
[No Author Listed] "Cannabidiol Therapy for Aicardi Syndrome" Aug. 2014, 4 pages.
[No Author Listed], Cover and Table of Contents, J Pharmacology and Exp Therapeutics, Feb. 2010, 332(2), 4 pages.
Alger, "Not Too Excited? Thank Your Endocannabinoids," Neuron., Aug. 2006, 51(4):393-395.
American Epilepsy Society, Three Studies Shed New Light on the Effectiveness of Cannabis in Epilepsy, Oct. 14, 2014, 2 pages.
Ames et al., "Anticonvulsant effect of cannabidiol," S. Afr Med. J., Jan. 1986, 69(1):14.
Arain et al., "Pregabalin in the Management of Partial Epilepsy," Neuropsychiatr Dis Treat., Aug. 2009, 5:407-413.
Arslan and Tirnaksiz, "Self-emulsifying Drug Delivery Systems," FABAD J Pharm Sci, 2013,38(1): 55-64.
AU Third Party Observations for Application No. AU2012314129, dated Mar. 19, 2015, 51 pages.
Avoli et al., "Cellular and molecular mechanisms of epilepsy in the human brain," Prog Neurobiol., 2005, 77(3):166-200.
Bakhsm, "Key Attributes of TKDL," Miftaah-al-Khazaain, 1930, 607-608 (with English translation).
Bancaud et al., "Proposal for Revised Clinical and Electroencephalographic Classification of Epileptic Seizures," Epilepsia, Aug. 1981, 22(4):489-501.
Banerjee et al., "Case Report: Aicardi syndrome: A report of five Indian cases," Neurology India, Mar. 2006, 54(1): 91-93.
Barker-Haliski et al, "How Clinical Development Can, and Should. Inform Translational Science," Neuron, Nov. 2014, 84: 582-593.
Benowitz et al., "Metabolic and Psychophysiologic studies of cannabidiol hexobarbital interaction," Clin Pharmacol Ther., 1980, 28(1):115-120.
Bertram, "The Relevance of Kindling for Human Epilepsy," Epilepsia, Apr. 2007, 48(Suppl. 2):65-74.
Bhatt et al., "Indigenous Plants in Traditional Healthcare System in Kedarnath Valley of Western Himalaya," Indian J Tradit Knowl., Apr. 2008, 7(2):300-310.
Bhattacharyya et al., "Modulation of mediotemporal and ventrostriatal function in humans by Delta9-tetrahydrocannabinol: a neural basis for the effects of *Cannabis sativa* on learning and psychosis," Arch Gen Psychiatry., 2009, 66:442-451.
BipolarHealthGroup.org [online], "Charlotte's Web Hemp Remedy," Bipolar Health Group, available on or before Sep. 6, 2017, retrieved on May 21, 2018, URL <http://bipolarhealthgroup.org/index.php/charlottes-web-hemp-remedy/>, 6 pages.
Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.
Bostanci et al., "The effects of octanol on penicillin induced epileptiform activity in rats: An in vivo study," Epilepsy Res., Jul. 27, 2006, 71(2-3):188-194.
Braida et al., "Post-ischemic treatment with cannabidiol prevents electroencephalographic flattening, hyper locomotion and neuronal injury in gerbils" Neuroscience Letters., 2003, 346:61-64.
Brust et al., "Marijuana use and the risk of new onset seizures," Trans Am Clin Climatol Assoc., 1992, 103:176-181.

Carlini et al., "Hypnotic and Antiepileptic Effects of Cannabidiol," J Clin Pharmacol., Aug.-Sep. 1981, 21(8-9 Suppl):417S-427S.
Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.
Charlotte's Web [online], "When to Expect Results from CW Hemp Oil", Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron and Dulac, "The Pharmacologic Treatment of Dravet Syndrome," Epilepsia, 2011, 52(Suppl. 2): 72-75.
Conry et al., "Clobazam in the treatment of Lennox-Gastaut syndrome," Epilepsia, May 2009, 50(5): 1158-1166.
Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.
Consroe et al., "Anticonvulsant drug antagonism of $\Delta^9$tetrahydrocannabinol-induced seizures in rabbits," Res Commun Chem Pathol Pharmacol., Jan. 1977, 16(1):1-13.
Consroe et al., "Anticonvulsant Interaction of Cannabidiol and Ethosuximide in Rats," J. Pharm. Pharmac., Aug. 1977, 29(8):500-501.
Consroe et al., "Anticonvulsant Nature of Marihuana Smoking," JAMA, Oct. 1975, 234(3):306-307.
Consroe et al., "Cannabidiol—Antiepileptic Drug Comparisons and Interactions in Experimentally Induced Seizures in Rats," J. Pharm. Exp. Therap., Apr. 1977, 201(1):26-32.
Consroe et al., "Effects of Cannabidiol on Behavioral Seizures Caused by Convulsant Drugs or Current in Mice," Eur J Pharm, Sep. 1982, 83(3-4):293-298.
Consroe et al., "Chapter 2: Therapeutic Potential of Cannabinoids in Neurological Disorders," Cannabinoids as Therapeutic Agents, R. Mechoulam ed., 1986, 21-49.
Cortesi et al., "Potential therapeutical effects of cannabidiol in children with pharmacoresistant epilepsy," Med Hypotheses., 2007, 68(4):920-921.
Cortez and Snead, "Chapter 10: Pharmacologic Models of Generalized Absence Seizures in Rodents," Models of Seizures and Epilepsy, 2006, 111-126.
Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., "Chronic Administration of Cannabidiol to Healthy Volunteers and Epileptic Patients," Pharmacology, 1980. 21(3):175-185.
Czapinski et al., "Mar. 17, 2008: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.
Dasa et al., "Key Attributes of TKDL: Ganja," Brhat Nighantu Ratnakara (Saligramanighantubhusanam), 1997, 6 pages (with English translation).
Davis and Ramsey, "Antiepileptic action of marihuana-active substances," Federation Proceedings., Mar. 1949, 8:284-285.
Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.
De Meijer, "Chapter 5: The Chemical Phenotypes (Chemotypes) of Cannabis," Handbook of Cannabis, ed. Roger G. Pertwee, 2014, 89-110.
De Oliveira, et al., "Anticonvulsant activity of β-caryophyllene against pentylenetetrazol-induced seizures," Epilepsy Behav, Mar. 2016, 56:26-31.

(56) References Cited

OTHER PUBLICATIONS

Deshpande et al., "Cannabinoid CBI Receptor Antagonists Cause Status Epilepticus-like Activity in the Hippocampal Neuronal Culture Model of Acquired Epilepsy," Neurosci Lett., Jan. 2007, 411: 11-16.
Devinsky et al., "Cannabidiol: Pharmacology and potential therapeutic role in epilepsy and other neuropsychiatric disorders," Epilepsia, 2014, 55(6):791-802.
Dravet, "The core Dravet syndrome phenotype," Epilepsia, Apr. 2011, 52(Suppl 2): 3-9.
Dreifus et al., "Proposal for Revised Clinical and Electroencephalographic Classification of Epileptic Seizures," Epilepsia, Aug. 1981, 22:489-501.
Dulac and Kaminska, "Use of Lamotrigine in Lennox-Gastaut and Related Epilepsy Syndromes," J. Child Neurolog., Nov. 1997, 12(S1): S23-S29.
Dulac et al., "Vigabatrin in Childhood Epilepsy," J. Child Neurolog., 1991, 6(S2): S30-S37.
Eadie, "Shortcomings in the current treatment of epilepsy," Expert Rev Neurother., Dec. 2012, 12(12): 1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
ElSohly and Gul, "Chapter 1: Constituents of *Cannabis sativa*," Handbook of Cannabis, 2014, ed. Roger G. Pertwee, 3-22.
Engel et al., "Chapter 1: What Should be Modeled?," In Models Seizure Epilepsy., 2006, 14 pages.
Engel, "Report of the ILAE Classification Core Group," Epilepsia, 2006, 47(9):1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5 , dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5 , dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EP11712658.1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm> , 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.

(56) References Cited

OTHER PUBLICATIONS

GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Examination Report in GB Appln. No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufinamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic," Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*Insys Development Company, Inc. v. GW Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc. v. GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc. v. GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc. v. GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*Insys Development Company, Inc. v. GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*Insys Development Company, Inc. v. GW Pharma Limited and Otsuka Pharmaceutical Co., Ltd.*, Deposition of H. Steve White, dated Dec. 13, 2016, 50 pages.
*Insys Development Company, Inc. v. GW Pharma Limited and Otsuka Pharmaceutical Co., Ltd.*, Final Written Decision in IPR2017-00503, U.S. Pat. No. 9,066,920, dated Jan. 3, 2019, 40 pages.
*Insys Development Company, Inc. v. GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*Insys Development Company, Inc. v. GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*Insys Development Company, Inc. v. GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc. v. GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc. v. GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
IUPHAR/BPS Guide to Pharmacology [online], "Entry for $\Delta$9-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.

(56) References Cited

OTHER PUBLICATIONS

Iuvone et al., "Neuroprotective Effect of Cannabidiol, a Non-psychoactive Component From *Cannabis sativa*, on β-amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol Use in Pediatric Treatment-Resistant Epilepsy", Apr. 2013, URL <https://www.thcint.com/uploads/1/9/3/7/19371199/cannabidiol_use_in_pediatric_epilepsy.pdf>, 1 page.
Jeavons et al., "Sodium Calproate in Treatment of Epilepsy," Br Med J., Jun. 15, 1974, 2(5919): 584-586.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The Cannabinoids as Potential Antiepileptics," J Clin Pharmacol., Aug.-Sep. 1981, 21:437S-448S.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Adiva, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).
Klitgaard et al., "Electrophysiological, neurochemical and regional effects of levetiracetam in the rat pilocarpine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):191-206.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kwan et al., "Definition of drug resistant epilepsy: consensus proposal by the ad hoc Task Force of the ILAE Commission on Therapeutic Strategies," Epilepsia, Jun. 2010, 51(6):1069-1077.
LeafScience.com [online], "What are the Highest CBD Strains?" Oct. 15, 2014, retrieved on Feb. 16, 2017, URL <www.leafscience.com/2014/10/15/highest-cbd-strains/>, 2 pages.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolaryngol Head Neck Surg, Mar. 2010, 142(3): 427-433.
Lindamood and Colasanti, "Effects of $\Delta^9$-Tetrahydrocannabinol and Cannabidiol on Sodium-Dependent High Affinity Choline Uptake in the Rat Hippocampus1," J Pharmacology Experimental Therapeutics, 1980, 213(2):216-221.
Long et al., "The Pharmacological actions of cannabidiol," Drugs of the Future, Jul. 2005, 30(7): 747-753.
Löscher and Schmidt, "Modern antiepileptic drug development has failed to deliver: ways out of the current dilemma." Epilepsia, Apr. 2011, 52(4):657-78.
Lowenstein "Chapter 363: Seizures and Epilepsy," Diseases of the Central Nervous System, 2008, 2498-2512.
Luttjohann et al., "A Revised Racine's scale for PTZ-induced seizures in rats," Physiology & Behavior, 2009, 98:579-586.
Lutz, "On-demand activation of the endocannabinoid system in the control of neuronal excitability and epileptiform seizures," Biochemical Pharmacology, Nov. 2004, 68(9):1691-1698.
Maa et al., "The Case for Medical Marijuana in Epilepsy," Epilepsia, Jun. 2014, 55(6):783-786.
Mackie, "Cannabinoid Receptors as Therapeutic Targets," Annu Rev Pharmacol Toxicol, 2006, 46:101-122.
Majoosi et al., "Key Attributes of TKDL: Saoot Baraae Sara," Kaamil-al-Sena'ah, Central Council for Research in Unani Medicine, 2005, 2 pages (with English translation).
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Mares et al., "Chapter 12: Electrical Stimulation-Induced Models of Seizures," Model of Seizures and Epilepsy, Asla Pitkänen, Philip A. Schwartzkroin & Solomon L. Moshé, eds., 2004, 153-159.
Martin et al., "Structure-Anticonvulsant Activity Relationships of Cannabidiol Analogs," National Institute on Drug Abuse, Research Monograph Series, 1987, 79:48-58.
Mattson et al., "Comparison of carbamazepine, phenobarbital, phenytoin, and primidone in partial and secondarily generalized tonic-clonic seizures," N Engl J Med, Jul. 18, 1985, 313(3):145-151.
Mattson et al., "Prognosis for total control of complex partial and secondary generalized tonic clonic seizures," Neurology, 1996, 47:68-76.
McCormick et al., "On the Cellular Network Bases of Epileptic Seizures," Annu Rev Physiol, 2001, 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., "Toward drugs derived from cannabis," Naturwissenschaften, Apr. 1978, 65(4): 174-179.
Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.
Merlis, "Proposal for an International Classification of the Epilepsies," Epilepsia, 1970, 11:114-119.
Miller et al., "Mapping genetic modifiers of survival in a mouse model of Dravet syndrome," Genes, Brain and Behavior, 2014, 13:163-172.
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 2007, 13:658-664.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Neto et al., "The role of polar phytocomplexes on anticonvulsant effects of leaf extracts of *Lippia alba* (Mill.) N.E. Brown chemotypes," J. Pharm Pharmacol, 2009, 61(7):933-939.
Ng et al., "Illicit Drug Use and the Risk of New-Onset Seizures," Am J Epidemiol, 1990, 132(1):47-57.
Oakley et al., "Dravet Syndrome Insights into pathophysiology and therapy from a mouse model of Dravet syndrome," Epilepsia, Apr. 2011, 52(Suppl. 2): 59-61.
Obay et al., "Antiepileptic effects of ghrelin on pentylenetetrazole-induced seizures in rats," Peptides, Jun. 2007, 28(6):1214-1219.
PCT International Preliminary Report on Patentability in International Appln. No. PCT/GB2010/051066, dated Jun. 9, 2011, 6 pages.

(56) References Cited

OTHER PUBLICATIONS

PCT International Preliminary Report on Patentability in International Appln. No. PCT/GB2012/052284, dated Dec. 12, 2013, 12 pages.
PCT International Preliminary Report on Patentability in International Appln. No. PCT/GB2015/051775, dated Aug. 10, 2016, 9 pages.
PCT International Preliminary Report on Patentability in International Appln. No. PCT/GB2015/053030, dated Apr. 18, 2017, 6 pages.
PCT International Preliminary Report on Patentability in International Appln. No. PCT/GB2016/051792, dated Sep. 1, 2017, 14 pages.
PCT International Search Report and Written Opinion in International Appln. No. PCT/GB2010/051066 dated Dec. 13, 2010, 8 pages.
PCT International Search Report and Written Opinion in International Appln. No. PCT/GB2011/050649, dated May 30, 2011, 15 pages.
PCT International Search Report and Written Opinion in International Appln. No. PCT/GB2012/052284, dated Nov. 16, 2012, 11 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2016/052340, dated Oct. 25, 2016, 12 pages.
PCT International Search Report and Written Opinion in International Appln. PCT/GB2017/051943, dated Sep. 12, 2017, 10 pages.
PCT International Search Report in International Appln. No. PCT/GB2012/050002, dated Feb. 24, 2012, 3 pages.
PCT Interntional Search Report and Written Opinion in International Appln. No. PCT/GB2017/051913, dated Sep. 15, 2017, 9 pages.
PCT Interntional Search Report and Written Opinion in International Appln. No. PCT/GB2017/051914, dated Sep. 12, 2017, 10 pages.
Pelliccia et al. [online], "Treatment with CBD in oily solution of drug-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett, Jun. 2007, 419(3): 253-257.
Pertwee, "Cannabinoid receptor ligands clinical and neuropharmacological considerations, relevant to future drug discovery and development," Expert Opin Investig Drugs, Jul. 2000, 9(7): 1553-1571.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol, 2008, 153(2):199-215.
Petrocellis et al., "Effects of cannabinoids and cannabinoid-enriched Cannabis extracts on TRP channels and endocannabinoid metabolic enzymes," British Journal of Pharmacology, 2011, 163: 1479-1494.
Pohl et al., "Effects of flunarizine on Metrazol-induced seizures in developing rats," Epilepsy Res, 1987, 1:302-305.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Porter et al., "Report of a Parent Survey of Cannabidiol-enriched Cannabis use in Pediatric Treatment-resistant Epilepsy," Epilepsy Behavior, Dec. 2013, 29(3): 574-577.
Potter, "Chapter 4: Cannabis Horticulture," Handbook of Cannabis, ed. Roger G. Pertwee, 2014, 65-88.
Pouton, "Lipid formulations for oral administration of drugs: non-emulsifying, self-emulsifying and 'self-microemulsifying' drug delivery systems," Eur. J Pharm Sci, Oct. 2000, 11(Supp. 2): S93-S98.
Press et al., "Parental reporting of response to oral cannabis extracts for treatment of refractory epilepsy," Epilepsy Behav, Apr. 2015, 45:49-52.
Pruitt et al., "Ethanol in Liquid Preparations Intended for Children," Padiatrics, Mar. 1984: 73(3): 405-407.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi-Goutieres syndrome," Official J Eur Paediatric Neurology Society, 2014, 18: 30-37.
Rauca et al., "The role of superoxide dismutase and a-tocopherol in the development of seizures and kindling induced by pentylenetetrazol-influence of the radical scavenger a-phenyl-N-tert-butyl nitrone," Brain Research, May 29, 2004, 1009(1-2):203-212.
Resstel et al., "5-HT$_{1A}$ receptors are involved in the cannabidiol-induced attenuation of behavioural and cardiovascular responses to acute restraint stress in rats," Br J Pharmacol, Jan. 2009, 156(1): 181-188.
Rosenkrantz et al., "Oral and Parenteral Formulations of Marijuana Constituents," J Pharm Sci, Jul. 1972, 61(7)1106-1112.
Rubio et al., "In Vivo Experimental Models of Epilepsy," Central Nervous System Agents in Medicinal Chemistry, 2010, 10:298-309.
Russo, "Taming THC: potential cannabis synergy and phytocannabinoid-terpenoid entourage effects," British J. of Pharm, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.
Stott et al., "Cannabinoids for the pharmaceutical industry," Euphytica, 2004, 140:83-93.
Strickley, "Solubilizing Excipients in Oral and Injectable Formulations," Table VIII, Pharmaceutical Research, Feb. 2004, 21(2): 201-230.
Swann., "The Effects of Seizures on the Connectivity and Circuitry of the Developing Brain," MRDD, 2004, 10(2):96-100.
Thomas et al., "Evidence that the Plant Cannabinoid Δ9-Tetrahydrocannabivarin is a Cannabinoid CB1 and CB2 Receptor antagonist," Br J Pharmacol, Dec. 2005, 146(7):917-926.

(56) References Cited

OTHER PUBLICATIONS

Thumma et al., "Influence of plasticizers on the stability and release of a prodrug of Δ9-tetrahydrocannabinol incorporated in poly (ethylene oxide) matrices," Eur J Pharmceutics and Biopharmaceutics, Oct. 2008, 70(2): 605-614.
Thurman et al., "Standards for epidemiologic studies and surveillance of epilepsy," Epilepsia, Sep. 2011, 52 Suppl 7: 2-26.
Thurstone, "Avoid Charlotte's Web for Epilepsy," Jun. 26, 2014, URL <http://drthurstone.com/charlotted-web-not-safest-option-epiliepsy-treatment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
Unimed Pharmaceuticals, Inc., "Marinol®," Jul. 2006 <https://www.accessdata.fda.gov/drugsatfda_docs/label/2006/018651s025s026lbl.pdf>, 11 pages.
Usami et al., "Synthesis and Pharmacological Evaluation in Mice of Halogenated Cannabidiol Derivatives," Chem Pharm Bull, Nov. 1999, 47(11):1641-1645.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jan. 21, 2017, 6 pages.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, Dec. 2008, 4(6): 1001-1019.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vollner et al., "Haschisch XX+ [Haschiscc XX+]: Cannabidivarin, a new hashish substance," Tetrahedron Letters, 1969, 10(3):145-147.
Wahle et al., "Development of Tolerance to the Anticonvulsant Effect of Valproate but not to Ethosuximide in a Rat Model of Absence Epilepsy," Eur J Pharma, May 1990, 181(1-2): 1-8.
Wallace et al., "Assessment of the role of CB1 receptors in cannabinoid anticonvulsant effects," European J Pharmacology, 2001, 428(1):51-57.
Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model of Epileptiform Activity," Proceedings of the British Pharm Society, Dec. 2006, retrieved on Mar. 1, 2017, URL <http://www.pA2online.org/abstract/abstract.jsp?abid=28533>, 1 page, Abstract Only.
Wikipedia.org [online], "Cannabinoid," Wikipedia, Apr. 2003, retrieved on Mar. 1, 2017, URL <https://en.wikipedia.org/wiki/Cannabinoid>, 15 pages.

Wingerchuk, "Cannabis for medical purposes: cultivating science, weeding out the fiction," Lancent, Jul. 2004, 364:315-316.
Yu et al., "Reduced sodium current in GABAergic interneurons in a mouse model of severe myoclonic epilepsy in infancy," Nature Neuroscience, Sep. 2006, 9(9): 1142-1149.
Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).
Zhao et al., "Chapter 27: Repetitive Seizures in the Immature Brain," Models of Seizures and Epilepsy, 2006, 341-350.
Zhornitsky and Potvin, "Cannabidiol in Humans—The Quest for Therapeutic Targets," Pharmaceuticals, 2012, 5:529-552.
Zuardi et al., "Cannabidiol, a *Cannabis sativa* constituent, as an antipsychotic drug," Brazilian Journal of Medicine and Biological Research, Apr. 2006, 39(4): 421-429.
Zuardi et al., "Cannabidiol: from an inactive cannabinoid to a drug with wide spectrum of action," Rev Bras Psiquiatr, 2008, 30(3): 271-80.
AU Re-examination report—standard patent for Australian Patent No. 2012204800, dated May 3, 2019, 7 pages.
Benowitz and Jones, "Cardiovascular and metabolic considerations in prolonged cannabinoid administration in man," J Clin Pharm, 1981, 21: 214S-223S.
Curia et al., "The pilocarpine model of temporal lobe epilepsy," J Neuroscience Methods, Jul. 2008, 172(2-4): 143-157.
GB Combined Search and Examination Report in GB Appln. No. GB1621480.1, dated Sep. 22, 2017, pages.
Grotenhermen, "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019, URL <http://s8a85e4d6fcfb04b6.jimcontent.com/download/version/1472724876/module/9873059694/name/Epilepsiebehandlung%20durch%20CBD.pdf>, 8 pages (with Machine translation).
Hill et al., "Cannabidivarin is anticonvulsant in mouse and rat," Br J Pharmacol, Dec. 2012, 167(8):1629-1642.
Karler et al., "The anticonvulsant activity of cannabidiol and cannabinol," Life Science, 1973, 13: 1527-1531.
Kruk-Slomka et al., "A comparison of mecamylamine and bupropion effects on memory-related responses induced by nicotine and scopolamine in the novel object recognition test in mice," Pharmacological Reports, Aug. 2014, 66(4): 638-646.
Kurz and Blass, "Use of dronabinol (delta-9-THC) in autism: a prospective single-case-study with an early infantile autistic child," 2010, Cannabinoids, 5(4): 4-6.
LaPrairie et al., "Cannabidiol is a negative allosteric modulator of the cannabidinoid CB1 receptor," British J Pharmacology, 2015, 172(20): 4790-4805.
PCT Interntaional Search Report and Written Opinion in International Appln. No. PCT/GB2017/053735, dated Mar. 14, 2018, 14 pages.
Physician's Desk Reference, 63rd Ed., 2009, 423-431, 2192-2194, 2639-2242, 3019-3022.
Sandyk et al., "Preliminary trial of cannabidiol in Huntington's Disease," Marihuana: An International Research Report, 1988, 157-162.
Thomas et al., "Cannabidiol displays unexpectedly high potency as an antagonist of CB1 and CB2 receptor agonists in vitro," British J Pharmacology, 2007, 150(5): 613-623.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Zamberletti et al., "Alterations of prefrontal cortex GABAergic transmission in the complex psychotic-like phenotype induced by adolescent delta-9-tetrahydrocannabinol exposure in rats," Neurobiology of Disease, Mar. 2014, 63: 35-47.
U.S. Appl. No. 16/467,639, filed Jun. 7, 2019, Geoffrey Guy.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.

(56) References Cited

OTHER PUBLICATIONS

[No Author Listed] GW Pharmaceuticals Provides Update on Orphan Program in Childhood Epilepsy for Epidolex, GW. Pharm. Available online Nov. 14, 2013, Retrieved Feb. 10, 2017.
[No Author Listed] "What are the Highest CBD Strains?" accessed Feb. 16, 2017, published Oct. 15, 2014.
[No Author Listed] "Cannabidiol Therapy for Aicardi Syndrome" Aug. 2014.
[No Author Listed] "Convulsive Disorders and Their Interference with Diiving," Medicos., Retrieved Feb. 10, 2017, Retrieved from internet: URL https://www.medicosporlaseguridadvial.com/en/clinical-subjects/neurologic-diseases/convulsive-disorders-and-their-interference-with-driving/, 2014.
[No Author Listed] Cannabinoid. Wikipedia. Retrieved on Jul. 9, 2015 from https://en. wikipedia.org/wiki/Cannabinoid.
[No Author Listed] Estimating the Maximum Safe Starting Dose in Initial Clinical Trials for Therapeutics in Adult Healthy Volunteers. FDA Guidance for Industry, Jul. 2005.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
Annex to the Communication-Opposition for Application No. 10734541. 5, dated Jan. 28, 2016.
Arzimanoglou et al. Epileptic Disord. 2011, 13, S3-S13 (Year: 2011).
"Cannabidiols: Potential Use in Epilepsy & Other Neurological Disorders." Cannabidol Conference at NYU School of Medicine, Oct. 2013. NYU Langone Health. Retreived from the Internet Nov. 2019.<URL: http://faces.med.nyu.edu/research-education/cannabidiol-conference>.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids.
Chiu et al., "The Influence of Cannabidiol and □9-Tetrahydrocannabinol on Cobalt Epilepsy in Rats," Epilepsia., 1979, 20:365-375.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. <http://faces.med.nyu.edu/research-education/cannabidiol-conference>.
Combined Search and Examination Report dated Jan. 4, 2012 for Application No. GB: 1116789.7.
Combined Search and Examination Report dated Mar. 25, 2011 for Application No. GB: 1100043.7.
Combined Search and Examination Report dated Sep. 5, 2014 for Application No. GB 1414813.4.
Combined Search and Examination Report Under Sections 17 and 18 (3) for International Application No. GB1121919.3, dated Feb. 29, 2012.
Combined Search and Examination Report Under Sections 17 and 18 (3) for International Application No. GB 141077 1 .8, dated Feb. 27, 2018.
Combined Search and Examination Report Under Sections 17 and 18 (3) for International Application No. GB 1418166.3, dated Jul. 2, 2015.
Combined Search and Examination Report Under Sections 17 and 18 (3) for International Application No. GB 1418170.5, dated Jul. 2, 2015.
Combined Search and Examination Report Under Sections 17 and 18 (3) for International Application No. GB 1418171.3, dated Jun. 29, 2015.
Combined Search and Examination Report Under Sections 17 and 18 (3) for International Application No. GB 1506550.1, dated Feb. 5, 2016.
Communication of a Notice of Opposition for Application No. 107342541.5 dated Dec. 17, 2014.
Communication Pursuant to Article 94(3) EPC in European Patent Application No. 10734541.5, dated Oct. 23, 2012.
Consroe et al., "Controlled clinical trial of cannabidiol in Huntington's Disease," Pharmacology Biochemistry & Behavior, 1991, 40:701-708.
Decision in IPR2017-00503 dated Jul. 7, 2017.
Decision in Opposition proceedings (Art. 101(3)(a) and 106(2) EPC in European Patent Application No. EP2448637, dated Dec. 15, 2016.
Declaration of Professor Anthony G.Marson in the Inter Partes Review of U.S. Pat. No. 9,066,920, Dated Dec. 13, 2016.
Declaration of Professor Leslie Benet in the Inter Partes Review of U.S. Pat. No. 9,066,920, Dated Nov. 22, 2016.
Declaration of Professor H. Steve White in the Inter Partes Review of U.S. Pat. No. 9,066,920, Dated Oct. 24, 2017.
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>.
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. <http://faces.med.nyu.edu/research-education/cannabidiol-conference>.
Dravet, The core Dravet syndrome phenotype. Epilepsia.52 Suppl 2:3-9. doi: 10.1111/j.1528-1167.2011.02994.x. (Year: 2011).
Drugs of the Future, 39(1): 49-56, Jan. 2014 notes Orphan Drug designation for CBD for Lennox-Gastaut Syndrome.
Engel, Report of the ILAE classification core group. Epilepsia. Sep. 2006;47(9): 1558-68.
Etienne de Meijer, "The Chemical Phenotypes (Chemotypes) of Cannabis," Chapter 5, Handbook of Cannabis, ed. Roger G. Pertwee, pp. 89-110 (2014).
Ex parte Edelstam, Appeal No. 2016/006358, mail date Jun. 21, 2017 (Year: 2017).
Ex parte Miller, Appeal 2009-011751, mail date Jul. 8, 2010 (Year: 2010).
Examination Report dated Mar. 18, 2014 for Application No. GB1100043.7.
Expert Statement of Vincenzo Di Marzo for Application No. EP10734541.5 dated Sep. 9, 2016.
Expert Statement of Professor Benjamin J. Whalley for Application No. EP10734541.5 dated Sep. 9, 2016.
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. <http://faces.med.nyu.edu/research-education/cannabidiol-conference>.
Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd.
Guerrini et al., "Lamotrigine and Seizure Aggravation in Severe Myoclonic Epilepsy," Epilepsia, 39(5):508-512, 1998.
Goodman & Gilman, The Pharmacological Basis of Therapeutics (Brunton, Laurence L.; Lazo, John S.; Parker, Keith, eds. (2006); (I Ith ed.), New York: McGraw-Hill. ISBN 0-07-142280-3); Chapter 19, Pharmacotherapy of the Epilepsies.
GWPhann [online], "GW Pharmaceuticals Announces Epidiolex(R) Receives Fast Track Designation from FD A for the Treatment of Dravet Syndrome," GW Pharmaceuticals Press Release, Jun. 6, 2014, retrieved on Mar. 1, 2017, URL https://www.gwphann com/about-us/news/gw-pharmaceuticals-announces-epidiolex%C2%AE-receives-fast-track-designation-fda-treatment.

(56) References Cited

OTHER PUBLICATIONS

*Insys Development Comp any, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018.
International Preliminary Report on Patentability in International Application No. PCT/GB2010/051066, dated May 5, 2011.
International Preliminary Report on Patentabiliiy for Application No. PCT/GB2015/053030, dated Apr. 18, 2017.
International Preliminary Report on Patentability for Application No. PCT/GB2012/052284, dated Mar. 29, 2014.
International Search Report and Written Opinion for Application No. PCT/GB2015/051775, dated Dec. 23, 2015.
International Search Report and Written Opinion for Application No. PCT/GB2015/051066, dated Jan. 1, 2012.
International Search Report and Written Opinion for Application No. PCT/GB2011/050649, dated Sep. 30, 2012.
International Search Report and Written Opinion dated Nov. 16, 2012 for Application No. PCT/GB2012/052284, dated Mar. 29, 2014.
International Search Report in International Application No. PCT/GB2010/051066, dated Jan. 6, 2011.
International Search Report in International Application No. PCT/GB2012/050002, dated Jul. 12, 2012.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013). Video published online. <http://faces.med.nyu.edu/research-education/cannabidiol-conference>.
Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. <http://faces.med.nyu.edu/research-education/cannabidiol-conference>.
Khan et al., Muheet-e-Azam, vol. II. 1887: 147. Persian. Exhibit 1.
Kwan et al., Definition of drug resistant epilepsy: consensus proposal by the ad hoc Task Force of the ILAE Commission on Therapeutic Strategies. Epilepsia. Jun. 2010;51(6):1069-77. doi:10.1111/j.1528-1167.2009.02397.x. Epub Nov. 3, 2009. Erratum in: Epilepsia. Sep. 2010;51(9): 1922.
LeafScience.com [online], "What are the Highest CBD Strains?" Oct. 15, 2014, retrieved on Feb. 16, 2017, URL www.leafscience.com/2014/10/15/highest-cbd-strains/.
Manno, "Status Epilepticus: Current Treatment Strategies," The Neurohospitalist. Jan. 2011, 1(1):23-31.
Mechoulam et al., "Cannabidiol: An Overview of Some Pharmacological Aspects," J Clin Pharmacol, 2002, 42:11S-19S.
Mechoulam et al., Toward drugs derived from cannabis. Naturwissenschaften. Apr. 1978;65(4): 174-9.
Models of Chemically-Induced Acute Seizures 127-152, 2006.
Notice of Allowance in U.S. Appl. No. 13/380,305, dated Dec. 10, 2014.
Notice of Allowance in U.S. Appl. No. 13/380,305, dated Mar. 19, 2015.
Notice of Appeal in European Patent No. EP2448637, dated Feb. 14, 2017.
Notice of Opposition to a Europearn Patent No. EP2448637, Dated Dec. 5, 2014.
Office Action in U.S. Appl. No. 13/380,305, dated Aug. 25, 2014.
Opponent Response to the Preliminary Opinion of the Opposition Division in European Patent No. EP2448637, dated Jun. 23, 2016.
Opponent Response dated to Sep. 9, Preliminary 2016, 25 Opinion pages of the Opposition Division in European Patent No. EP2448637, dated Sep. 9, 2016.
Opponent Response to the Written Submissions in European Patent No. EP2448637, dated Oct. 12, 2016.
Opponent Response to the Written Submissions in European Patent No. EP2448637, dated Oct. 20, 2016.
Opponent Response to the Written Submissions in European Patent No. EP2448637, dated Nov. 4, 2016.
Patent Owners' Preliminary Response for IPR2017-00503 dated Apr. 11, 2017.
PCT International Preliminary Report on Patentability in International Appln. No. PCT/US2017/050868, dated Jun. 18, 2019.
PCT International Search Report and Written Opinion in International Appln. No. PCT/US2017/050868, dated Jun. 21, 2018.
Petition for Inter Partes Review U.S. Pat. No. 9,066,920 dates Dec. 16, 2016.
Petitioner's Reply to Patent Owner's Response in Inter Partes Review No. IPR2017-00503, filed Jan. 19, 2018.
Resstel et al., 5-HT1A receptors are involved in the cannabidiol-induced attenuation of behavioural and cardiovascular responses to acute restraint stress in rats. Br J Pharmacol. Jan. 2009;156(1): 181-8.
Reply of the Patent Proprietor to the Notice(s) of Opposition in European Patent No. 2448637, dated May 28, 2015, 12 pages.
Reply to Communication from the examining Division in Eurppean Patent Application No. 10734541.5 dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016, 13 pages.
Reply to Opponent's Written Submission in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Rohrback, Brian G., Ph.D, MBA President of Infometrix, Inc. presents his talk on "Assays of Cannabinoids," at NYU School of Medicine's Cannabidiol Conference (Oct. 4, 2013). Video published online. <http://faces.med.nyu.edu/research-education/cannabidiol-conference>.
Rosenberg et al., "Cannabinoids and Epilepsy," Neurotherapeutics, Oct. 2015, 12(4): 747-768.
Silva, R. et al. Can J. Neurol. Sci. 2006 vol. 33 pp. 783-786.
Statement of Opposition for EP10734541.5, mailed Dec. 5, 2014.
Swann et al., The effects of seizures on the connectivity and circuitry of the developing brain. Ment Retard Dev Disabil Res Rev. 2004; 10(2):96-100.
Stafstrom et al., "Models of Pediatric Epilepsies: Strategies and Opportunities," Epilepsia, vol. 47, No. 8, 2006.
Statement of Grounds of Appeal for European Application No. 10734541.5 in the name of GW Pharma and Otsuka Pharmaceutical Co. Limited Appellant/Opponent: lnsys Therapeutics Inc., dated Apr. 21, 2017.
Statement of Grounds of Appeal for European Application No. 10734541.5 on behalf of the Proprietors: GW Pharma Limited and Otsuka Pharmaceutical Co Limited, dated Apr. 12, 2017.
Tanya Lewis, Mystery Mechanisms, The Scientist Magazine, Jul. 29, 2016.
Transcript of Dr. H. Steven White's deposition, dated Dec. 29, 2017.
Third Party Observations for Application No. AU20 1 2314128, mailed Mar. 19, 2015.
Third Party Observations for Application No. EP10734541.5, mailed Apr. 3, 2017.
Third Party Observations for Application No. EP1712658.1, mailed Nov. 22, 2013.
Wallace et al., "Pharmacotherapy forDravet Syndrome," Pediatr. Drugs, 18:197-208 (2016).
Wallace et al., Assessment of the role of CB 1 receptors in cannabinoid anticonvulsant effects. Eur J Pharmacol. Sep. 28, 2001;428(1):51-7.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>.

(56) References Cited

OTHER PUBLICATIONS

"When to Expect Results from CW Hemp Oil", downloaded Sep. 5, 2017, https://www.cwhemp.com/blog/expecting-results-from-hemp.

Wikipedia.org [online], "Cannabinoid," Wikipedia, Apr. 2003, retrieved on Mar. 1, 2017, URL <https://en.wikipedia.org/wiki/Cannabinoid>.

Expert Statement of Professor Anthony G. Marson for for Application No. EP10734541.5, dated Jun. 14, 2016.

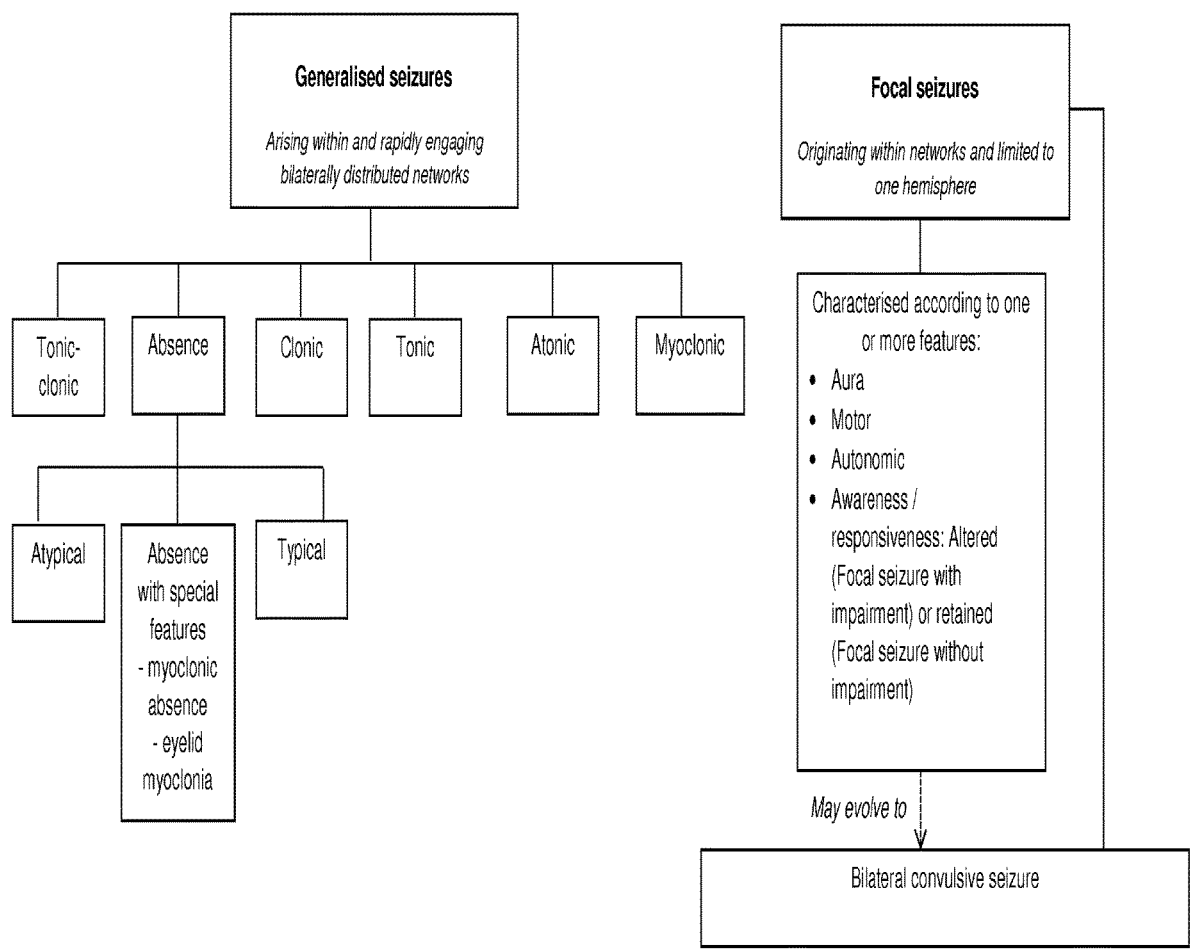

USE OF CANNABINOIDS IN THE TREATMENT OF EPILEPSY

FIELD OF THE INVENTION

The present invention relates to the use of cannabidiol (CBD) in the treatment of atonic seizures. In one embodiment the patients suffering from atonic seizures are children and young adults. CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types.

In these patients treatment with CBD reduced the occurrence of atonic seizures by greater than 50% in a large proportion, namely 63%, of patients. This was surprising given that the proportion of patients benefiting from a greater than 50% reduction in total seizures was significantly less, (46%), in all subjects treated.

Preferably the CBD used is in the form of a highly purified extract of *cannabis* such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD may be given concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace Secondary Generalized Seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Atonic seizures involve the loss of muscle tone, causing the person to fall to the ground. These are sometimes called 'drop attacks' and are usually brief (less than 15 seconds). Atonic seizures can occur without warning while standing, sitting and walking and the patient often suffers from trauma due to falling.

Atonic seizures are often associated with Lennox-Gastaut Syndrome but also occur, and may be symptomatic of other types of epileptic syndromes including: Tuberous Sclerosis Complex; Dravet Syndrome; Doose Syndrome; Aicardi syndrome; CDKL5 and Dup15q.

Epileptic syndromes often present with many different types of seizure and identifying the types of seizure that a patient is suffering from is important as many of the standard AED's are targeted to treat or are only effective against a given seizure type/sub-type.

One such childhood epilepsy syndrome is Lennox-Gastaut syndrome. Lennox-Gastaut syndrome is a severe form of epilepsy. Seizures usually begin before the age of 4. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods.

Most children with Lennox-Gastaut syndrome experience some degree of impaired intellectual functioning or information processing, along with developmental delays, and behavioural disturbances.

Lennox-Gastaut syndrome can be caused by brain malformations, perinatal asphyxia, severe head injury, central nervous system infection and inherited degenerative or metabolic conditions. In 30-35 percent of cases, no cause can be found.

The first line treatment for atonic seizures, including the treatment of atonic seizures in patients with Lennox-Gastaut syndrome usually comprises a broad spectrum AED, such as sodium valproate often in combination with lamotrigine. Other AED that may be considered include rufinamide, felbamate, clobazam and topiramate.

AED such as carbamezapine, gabapentin, oxcarbazepine, pregabalin, tiagabineor and vigabatrin are contra-indicated in atonic seizures.

Common AED defined by their mechanisms of action are described in the following tables:

TABLE 1

Examples of narrow spectrum AED

| Narrow-spectrum AED | Mechanism | Indication |
| --- | --- | --- |
| Phenytoin | Sodium channel | Complex partial<br>Tonic-clonic |
| Phenobarbital | GABA/Calcium channel | Partial seizures<br>Tonic-clonic |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
| --- | --- | --- |
| Valproic acid | GABA/Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures<br>Atonic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
| --- | --- | --- |
| Clobazam | GABA | Adjunctive therapy in complex partial seizures<br>Status epilepticus<br>Myoclonic<br>Myoclonic-absent<br>Simple partial<br>Complex partial<br>Absence seizures<br>Lennox-Gastaut syndrome |
| Stiripentol | GABA | Severe myoclonic epilepsy in infancy (Dravet syndrome) |

From these tables it can be seen that there is only one drug currently approved for use in the treatment of atonic seizures, namely clonazepam. This medication works by the GABA mechanism.

Over the past forty years there have been a number of animal and human studies on the use of the non-psychoactive cannabinoid cannabidiol (CBD) to treat seizures.

A study in 1978 provided 200 mg/day of pure CBD to four adult patients, two of the four patients became seizure free, whereas in the remainder, seizure frequency was unchanged (Mechoulam and Carlini, 1978).

Cunha et al. reported that administration of CBD to eight adult patients with generalized epilepsy resulted in a marked reduction of seizures in 4 of the patients (Cunha et al., 1980) and Consroe et al., (1982) determined that CBD was able to prevent seizures in mice after administration of pro-convulsant drugs or an electric current.

In contrast to the studies described above, an open label study reported that 200 mg/day of pure CBD was ineffective in controlling seizures in twelve institutionalized adult patients (Ames and Cridland, 1986).

All of the studies described above focused on the treating subjects suffering from generalised epilepsy and did not look at the treatment of specific seizure sub-types.

More recently, WO 2011/001169 describes the use of CBD in the treatment of focal seizures, WO 2012/093255 describes the use of CBD in combination with standard anti-epileptic drugs in the treatment of epilepsy and WO 2013/045891 describes a composition comprising CBD and CBDV for use in the treatment of epilepsy.

In November 2013 the company GW Pharmaceuticals made a press release to state that they were intending to treat Dravet Syndrome with CBD as it had received orphan drug designation. The company made a further press release in February 2014 that that they were intending to treat Lennox-Gastaut Syndrome with CBD as it had also received orphan drug designation.

Again the rationale was to treat a disease as opposed to the type of seizure that the subject experienced.

It has additionally been suggested that *cannabis* which is enriched in CBD may be efficacious in the treatment of epilepsy. A case study of a child with Lennox-Gastaut syndrome showed improvement in seizure frequency after treatment with CBD in an oily solution was reported in 2005 (Pelliccia et al. 2005).

Porter and Jacobson (2013) report on a parent survey conducted via a Facebook group which explored the use of *cannabis* which was enriched with CBD in children with treatment-resistant epilepsy. It was found that sixteen of the 19 parents surveyed reported an improvement in their child's epilepsy. The children surveyed for this paper were all taking *cannabis* that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported. Providing children with TRE with a *cannabis* extract that comprises THC, which has been described as a pro-convulsant (Consroe et al., 1977), at a potentially psychoactive dose of 0.8 mg/kg/day, is a concern.

In addition a paper published in June 2014 describes the use of a high-CBD strain to treat a patient with Dravet Syndrome; the patient's seizure frequency was stated to be reduced by the treatment (Maa et al. 2014).

A document published after the priority application was filed discloses the use of CBD in the treatment of refractory epilepsy in the treatment of Tuberous Sclerosis Complex in patients having focal onset seizures (Geffrey et al., 2014).

Whilst the potential of *cannabis* and the cannabinoids, including CBD, to treat epilepsy has been rekindled, to date there has been little in the way of real data to support its efficacy in patients.

The applicant has found that CBD shows significant efficacy in reducing atonic seizures, by greater than 50% in a large proportion, namely 63%, of patients. By way of comparison the proportion of patients benefitting from a greater than 50% reduction in total seizures was significantly less, (46%), in all subjects treated.

It is additionally worth noting that the patients being treated were treatment resistant to existing AED and so consequently these figures are even the more remarkable.

BRIEF SUMMARY OF THE DISCLOSURE

In accordance with a first aspect of the present invention there is provided cannabidiol (CBD) for use in the treatment of atonic seizures.

Preferably the atonic seizures are treatment-resistant.

Preferably the atonic seizures associated with Lennox-Gastaut Syndrome; Tuberous Sclerosis Complex; Dravet Syndrome; Doose Syndrome; Aicardi syndrome, CDKL5 or Dup15q.

In one embodiment the CBD is for use in combination with one or more concomitant anti-epileptic drugs (AED).

In a further embodiment the CBD is present as a highly purified extract of *cannabis* which comprises at least 95% (w/w) CBD, more preferably 98% (w/w) CBD. Preferably the extract comprises less than 0.15% THC. More preferably the extract further comprises up to 1% CBDV.

In an alternative embodiment the wherein the CBD is present as a synthetic compound.

In a further embodiment of the invention the one or more AED is selected from the group consisting of: clobazam; clonazepam, levetiracetam; topiramate; stiripentol; phenobarbital; lacsamide; valproic acid; zonisamide; perampanel; and fosphenytoin.

Preferably the number of different anti-epileptic drugs that are used in combination with the CBD is reduced. Alternatively the dose of the one or more anti-epileptic drugs that are used in combination with the CBD is reduced.

Preferably the dose of CBD is greater than 5 mg/kg/day.

In accordance with a second aspect of the present invention there is provided a method of treating atonic seizures comprising administering cannabidiol (CBD) to a subject.

In accordance with a third aspect of the present invention there is provided a composition for use in the treatment of atonic seizures characterised by atonic seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25/mg/ml and 100 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame q.s. to 1.0 ml.

BRIEF DESCRIPTION OF THE DRAWINGS

FIG. 1 shows the ILEA 2010 proposal for revised terminology for organization of seizures and epilepsies.

DEFINITIONS

Definitions of some of the terms used to describe the invention are detailed below:

The cannabinoids described in the present application are listed below along with their standard abbreviations.

TABLE 4

Cannabinoids and their abbreviations

| CBD | Cannabidiol |

TABLE 4-continued

| Cannabinoids and their abbreviations | | |
|---|---|---|
| CBDA | Cannabidiolic acid | |
| CBDV | Cannabidivarin | |
| CBDVA | Cannabidivarinic acid | |
| THC | Tetrahydrocannabinol | |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Atonic Seizures" are defined as a convulsive type of epileptic seizure which causes the muscles to relax and the patient to flop or fall.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

CBD Specification

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° C. (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0 % |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT - Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereo-chemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis. The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
|---|---|---|---|
| Cannabidiol (CBD) | 25 mg/ml or 100 mg/ml | Active | In-house |
| Anhydrous ethanol | 79.0 mg/ml* | Excipient | Ph.Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph.Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified *cannabis* extract comprising cannabidiol (CBD) in an expanded access treatment program in children with TRE.

Example 1: Efficacy of Cannabidiol Reducing Atonic Seizures in Children and Young Adults with Intractable Epilepsy Materials and Methods Of 137 children and young adults with severe, childhood onset treatment-resistant epilepsy (TRE), twenty-seven suffered from epilepsy that was characterised by atonic seizures. These subjects were tested with a highly purified extract of cannabidiol (CBD) obtained from a *cannabis* plant. All subjects presented with atonic type seizures, often in addition to other seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome; Doose Syndrome; Aicardi syndrome, CDKL5 and Dup15q.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4 weeks of CBD therapy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Results

There were 27 children and young adult patients all of whom suffered from atonic seizures received treatment with CBD for at least 12 weeks.

A summary of the 50% responders, based on 12 weeks of treatment are summarized in Table 7 below.

TABLE 7

Summary of 50% responders after 12 weeks of treatment for atonic seizures

|  | Atonic seizures (n = 27) | Total seizures (n = 137) |
|---|---|---|
| >50% reduction in seizures | 63% (n = 17) | 46% (n = 63) |
| <50% reduction in seizures | 37% (n = 10) | 54% (n = 74) |

Table 7 shows that after 3 months of therapy, a remarkable 63% of patients had an equal to or greater than >50% reduction in atonic seizures, these data infer that the CBD is very effective at reducing this type of seizure.

CONCLUSIONS

These data indicate that CBD significantly reduces the number of atonic seizures in a high proportion of patients that do not respond well to existing AED.

It was surprising that in this group of patients which are treatment-resistant such a high number were able to gain an effect. The fact that nearly two thirds of the patients (63%) benefitted from at least a fifty percent reduction in the number of atonic seizures that they suffered from was remarkable.

Furthermore when these data are compared to the other sub-types of generalised seizure, it can clearly be seen that CBD was able to selectively reduce the occurrence of atonic seizures. Table 8 below details these findings.

TABLE 8

Summary of 50% responders after 12 weeks of treatment for all seizure sub-types

|  | Atonic seizures (n = 27) | Tonic seizures (n = 45) | Tonic-clonic seizures (n = 65) | Clonic seizures (n = 8) | Myoclonic seizures (n = 30) | Absence seizures (n = 28) |
|---|---|---|---|---|---|---|
| >50% reduction in seizures | 63% (n = 17) | 49% (n = 22) | 43% (n = 28) | 50% (n = 4) | 43% (n = 13) | 64% (n = 18) |
| <50% reduction in seizures | 37% (n = 10) | 51% (n = 23) | 37% (n = 37) | 50% (n = 4) | 57% (n = 17) | 36% (n = 10) |

From Table 8 it can be seen that when the number of atonic seizures recorded is compared with other generalised seizure types such as tonic seizures (49% of patients experienced a greater than 50% reduction in seizure), tonic-clonic seizures (43% of patients experienced a greater than 50% reduction in seizure), and myoclonic seizures (43% of patients experienced a greater than 50% reduction in seizure) the fact that nearly two thirds (63%) of patients experiencing atonic seizures had a greater than 50% reduction in the number of seizures that occurred is very surprising.

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." *Expert Review of Neurotherapeutics* 12 (12): 1419-27.

Geffrey A, Pollack S, Paolini J, Bruno P, Thiele E (2014) "Cannabidiol (CBD) treatment for refractory epilepsy in Tuberous Sclerosis Complex (TSC)." American Epilepsy Society Annual Meeting. 5-9 Dec. 2014.

Kwan P, Arzimanoglou A, Berg A T, Brodie M J, Hauser W A, Mathern G, Moshé S L, Perucca E, Wiebe S, French J. (2009) "Definition of drug resistant epilepsy: Consensus proposal by the ad hoc Task Force of the ILAE Commission on Therapeutic Strategies." *Epilepsia*.

Maa E and Figi P (2014). "The case for medical marijuana in epilepsy", Epilepsia 55(6):783-786

Mechoulam R and Carlini E A (1978). "Toward drugs derived from *cannabis*." Die naturwissenschaften 65:174-9.

Pelliccia A, Grassi G, Romano A, Crocchialo P (2005). "Treatment with CBD in oily solution of drug resistant paediatric epilepsies". Congress of *Cannabis* and the Cannabinoids, Leiden, The Netherlands. International Association for *Cannabis* as a Medicine. p 14.

Porter B E, Jacobson C (December 2013). "Report of a parent survey of cannabidiol-enriched *cannabis* use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia*. 52 Suppl 7: 2-26

The invention claimed is:

1. A method of treating drop seizures in a patient with Lennox-Gastaut syndrome or Dravet syndrome, comprising administering to the patient cannabidiol (CBD), wherein the CBD has a purity of at least 95% (w/w), and the CBD is administered at a dose of 5 mg/kg/day, and then the dose is increased by 2 to 5 mg/kg increments, up to 25 mg/kg/day.

2. The method of claim 1, wherein the CBD comprises Δ9-tetrahydrocannabinol (THC).

3. The method of claim 2, wherein the CBD comprises not more than 0.15% (w/w) Δ9-tetrahydrocannabinol (THC).

4. The method of claim 1, wherein the dose of the CBD is increased to a dose ranging from 10 mg/kg/day to 25 mg/kg/day.

5. The method of claim 1, wherein the dose of the CBD is increased to a dose ranging from 10 mg/kg/day to 20 mg/kg/day.

6. The method of claim 1, wherein the CBD has a purity of at least 98% (w/w).

7. The method of claim 1, wherein the dose of the CBD is increased to about 25 mg/kg/day.

8. The method of claim 1, wherein the dose of the CBD is increased to about 10 mg/kg/day.

9. The method of claim 1, wherein the dose of the CBD is increased to about 12 mg/kg/day.

10. The method of claim 1, wherein the dose of the CBD is increased to about 14 mg/kg/day.

11. The method of claim 1, wherein the dose of the CBD is increased to about 15 mg/kg/day.

12. The method of claim 1, wherein the dose of the CBD is increased to about 18 mg/kg/day.

13. The method of claim 1, wherein the dose of the CBD is increased to about 20 mg/kg/day.

14. The method of claim 1, wherein the patient has Lennox-Gastaut Syndrome.

15. The method of claim 1, wherein the patient has Dravet syndrome.

16. The method according to claim 1, wherein the CBD is administered in combination with one or more concomitant anti-epileptic drugs (AED) to the patient at a recommended therapeutic dose.

17. The method according to claim 16, wherein the one or more AED is selected from the group consisting of: clobazam; clonazepam, levetiracetam; topiramate; stiripentol; phenobarbital; lacosamide; valproic acid; zonisamide; perampanel; and fosphenytoin.

18. The method according to claim 16, wherein the number of different AED that are administered in combination with the CBD to the patient is reduced.

19. The method according to claim 16, wherein the recommended therapeutic dose of the one or more AED that are administered in combination with the CBD is reduced from the recommended therapeutic dose without CBD.

20. A method of treating drop seizures in a patient with Lennox-Gastaut syndrome or Dravet syndrome, comprising administering to the patient cannabidiol (CBD), wherein the CBD has a purity of at least 95% (w/w), and wherein the CBD is administered at a dose ranging from 5 mg/kg/day to 20 mg/kg/day.

21. The method of claim 20, wherein the CBD has a purity of at least 98% (w/w).

22. The method of claim 20, wherein the dose of the CBD is from 10 mg/kg/day to 20 mg/kg/day.

23. The method of claim 20, wherein the dose of the CBD is about 10 mg/kg/day.

24. The method of claim 20, wherein the dose of the CBD is about 12 mg/kg/day.

25. The method of claim 20, wherein the dose of the CBD is about 14 mg/kg/day.

26. The method of claim 20, wherein the dose of the CBD is about 15 mg/kg/day.

27. The method of claim 20, wherein the dose of the CBD is about 18 mg/kg/day.

28. The method of claim 20, wherein the dose of the CBD is about 20 mg/kg/day.

29. The method of claim 20, wherein the CBD comprises not more than 0.15% (w/w) Δ9-tetrahydrocannabinol (THC).

30. The method of claim 20, wherein the CBD is administered at a starting dose of 5 mg/kg/day, and then the dose is increased by 2 to 5 mg/kg increments.

31. The method of claim 20, wherein the patient has Lennox-Gastaut Syndrome.

32. The method of claim 20, wherein the patient has Dravet syndrome.

* * * * *

UNITED STATES PATENT AND TRADEMARK OFFICE
CERTIFICATE OF CORRECTION

Page 1 of 1

PATENT NO. : 10,849,860 B2
APPLICATION NO. : 16/198141
DATED : December 1, 2020
INVENTOR(S) : Geoffrey Guy et al.

It is certified that error appears in the above-identified patent and that said Letters Patent is hereby corrected as shown below:

On the Title Page

References Cited, U.S. Patent Documents, Second column:
"1,099,252    A1    10/2018 Guy et al."
Should read:
-- 10,092,525    A1    10/2018 Guy et al. --

References Cited, U.S. Patent Documents, Second column:
"1,011,184    A1    10/2018 Guy et al."
Should read:
-- 10,111,840    A1    10/2018 Guy et al. --

References Cited, U.S. Patent Documents, Second column:
"1,013,709    A1    10/2018 Guy et al."
Should read:
-- 10,137,095    A1    10/2018 Guy et al. --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*